United States Patent [19]

Theeuwes

[11] Patent Number: 4,740,200
[45] Date of Patent: * Apr. 26, 1988

[54] INTRAVENOUS SYSTEM FOR DELIVERING A BENEFICIAL AGENT

[75] Inventor: Felix Theeuwes, Los Altos, Calif.

[73] Assignee: ALZA Corporation, Palo Alto, Calif.

[*] Notice: The portion of the term of this patent subsequent to Mar. 27, 2001 has been disclaimed.

[21] Appl. No.: 702,293

[22] Filed: Feb. 15, 1985

Related U.S. Application Data

[60] Division of Ser. No. 310,047, Oct. 9, 1981, Pat. No. 4,511,353, which is a continuation-in-part of Ser. No. 283,007, Jul. 13, 1981, abandoned.

[51] Int. Cl.⁴ ............................................. A61M 37/00
[52] U.S. Cl. ........................................ 604/85; 604/56; 604/92; 604/406
[58] Field of Search .................................. 604/82–85, 604/56, 72, 246, 406, 251–255

[56] References Cited

U.S. PATENT DOCUMENTS

| | | | |
|---|---|---|---|
| 3,001,525 | 9/1961 | Hendricks | 128/214 |
| 3,305,446 | 2/1967 | Bechtol et al. | 167/72 |
| 3,760,984 | 9/1973 | Theeuwes | 222/95 |
| 3,797,494 | 3/1974 | Zaffaroni | 128/268 |
| 3,845,770 | 11/1974 | Theeuwes et al. | 128/260 |
| 3,848,603 | 11/1974 | Throner | 128/349 |
| 3,854,480 | 12/1974 | Zaffaroni | 128/260 |
| 3,921,635 | 11/1975 | Gauthier | 128/214 R |
| 3,921,636 | 11/1975 | Zaffaroni | 128/260 |
| 3,941,126 | 3/1976 | Dietrick et al. | 128/214 |
| 3,948,254 | 4/1976 | Zaffaroni | 128/127 |
| 3,993,072 | 11/1976 | Zaffaroni | 128/260 |
| 3,993,073 | 11/1976 | Zaffaroni | 128/260 |
| 3,995,631 | 12/1976 | Higuchi et al. | 128/260 |
| 4,177,256 | 12/1979 | Michaels et al. | 424/22 |
| 4,203,439 | 5/1980 | Theeuwes | 128/260 |
| 4,233,973 | 11/1980 | Shukla | 128/214 R |
| 4,323,457 | 4/1982 | Sun et al. | 210/645 |
| 4,465,471 | 8/1984 | Harris et al. | 604/56 |

FOREIGN PATENT DOCUMENTS 497181 9/1969 Switzerland.
982107 9/1963 United Kingdom.

Primary Examiner—C. Fred Rosenbaum
Assistant Examiner—Mario Costantino
Attorney, Agent, or Firm—Paul L. Sabatine; Edward L. Mandell; Shelley G. Precivale

[57] ABSTRACT

A formulation chamber is disclosed comprising a wall surrounding a lumen containing a device for delivering a beneficial agent. The chamber has an inlet for admitting a fluid into the chamber and an outlet for letting an agent formulation leave the chamber. The chamber is adapted for use in an intravenous delivery system for delivering an agent formulation to a patient.

7 Claims, 3 Drawing Sheets

INTRAVENOUS SYSTEM FOR DELIVERING A BENEFICIAL AGENT

CROSS REFERENCE TO RELATED APPLICATION

This application is a division of copending patent application U.S. Ser. No. 310,047, filed on Oct. 9, 1981, now U.S. Pat. No. 4,511,353 issued Apr. 16, 1985, which application is a continuation-in-part of patent application U.S. Ser. No. 283,007 filed on July 13, 1981, now abandoned, which applications are incorporated herein by reference and benefit is claimed of their filing date. This application is copending with an application identified as ARC 801 CIP, now Ser. No. 312,491 filed Oct. 19, 1981 issued U.S. Pat. No. 4,552,555 on Nov. 12, 1985. All of the applications are assigned to the ALZA Corporation of Palo Alto, Calif.

TECHNICAL FIELD

This invention pertains to an intravenous delivery system, and to a drug formulation chamber containing an agent delivery device. The invention relates also to a method of administering intravenously an agent formulation, and to a method for forming the agent formulation.

BACKGROUND OF THE INVENTION

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solution, electrolyte solution and saline. Generally the liquids are administered from an intravenous delivery system having a container suspended above the patient, with the liquid flowing through a catheter hypodermic needle set to the patient.

The administration of liquids intravenously is a valuable and important component that contributes to the optimal care of the patient; however, it does not provide a satisfactory means and method for administering concomitantly therewith a beneficial agent. Presently, a beneficial agent is administered intravenously by (1) temporarily removing the intravenous system administering the agent to the patient followed by reinserting the intravenous system into the patient; (2) the agent is added to the liquid in the container and then carried by the flow of the liquid to the patient; (3) agent is added to a liquid in a separate container called a partial fill that is connected to the primary intravenous line through which line the agent is carried by the flow of liquid to the patient; (4) agent is contained in a piggyback vial into which is introduced an intravenous fluid, with the vial subsequently connected to the primary line through which the agent is administered to a patient, or (5) agent is administered by a pump that exerts a force on a liquid containing agent for intravenously administering the liquid containing the agent. While these techniques are used, they have major disadvantages. For example, they often require preformulation of the agent medication by the hospital pharmacist or nurse, they require separate connections for joining the primary intravenous line that further complicates intravenous administration, the use of pumps can produce pressures that can vary at the delivery site and the pressure can give rise to thrombosis, and the rate of agent delivery to the patient often is unknown as it is not rate-controlled agent delivery but delivery dependent on the flow of fluid administered over time.

In view of this presentation, it is apparent a critical need exists in the field of intravenous delivery for a rate-controlling means for administering a beneficial agent in intravenous delivery systems.

DISCLOSURE OF THE INVENTION

Accordingly, a principal object of this invention is to provide an intravenous delivery system comprising means for admitting an agent at a rate controlled by the means into an intravenous fluid for optimizing the care of a human whose prognosis benefits from intravenous delivery.

Another object of the invention is to provide an intravenous delivery system comprising an agent formulation chamber comprising an agent delivery device for admitting an agent at a rate controlled by the delivery device into an intravenous fluid for optimizing the care of a patient on intravenous delivery.

Another object of the invention is to provide an agent formulation chamber adapted for use with an intravenous delivery system and which chamber houses an agent delivery device for admitting an agent at a rate essentially controlled by the device into an intravenous fluid admitted into the chamber.

Another object of the invention is to provide an intravenous therapeutic system comprising a container and a drug formulation chamber that houses a device for delivering a drug at a rate governed by the device into a medical fluid that flows from the container into the chamber and then to a drug recipient.

The invention concerns both an intravenous delivery system comprising an agent formulation chamber and the agent formulation chamber. The chamber contains an agent formulation, wherein an agent originally present in a delivery means present in the chamber is released at a rate controlled by the delivery means. The agent on its release is formulated in situ with an intravenous fluid that enters the chamber with the agent released at a controlled rate that is essentially independent of the volume rate of an intravenous fluid entering the formulation chamber, and then infused into a recipient. The expression delivery means, as used herein, generically denotes a means or a system for storing and delivering a beneficial agent at a rate controlled by the means to establish a beneficial or a therapeutic need. The means, is presently preferred embodiments, are designed and manufactured as an agent delivery device, which device also is a rate-controlled dosage form of the agent. The delivery device or dosage forms stores an amount of agent for executing a prescribed beneficial program, and it provides for the preprogrammed, unattended delivery of a beneficially or a therapeutically effective amount of the agent to produce a beneficial or therapeutic result. The delivery device, or the dosage form, are adapted for easy placement and retention in the formulation chamber, and they substantially maintain their physical and chemical integrity during their release history. The expression beneficial agent generically denotes a substance that produces a beneficial or a therapeutic result, such as a drug, a carbohydrate, and/or the like. The term fluid or liquid denotes a fluid that can be administered parenterally including intravenously comprising pharmaceutically acceptable fluids that are also a pharmaceutically acceptable carrier for the agent. The invention also is an intravenous therapeutic system for administering a liquid drug formulation, wherein the liquid drug formulation is formulated in situ. The intravenous delivery system generically comprises in combination:
(a) a container for storing a pharmaceutically acceptable liquid carrier for the agent;
(b) an agent formulation chamber comprising: an inlet that permits communication with the container to let a liquid carrier flow from the container into the formulation chamber; and an outlet through which the liquid exits the chamber;
(c) an agent delivery means in the chamber, which means is a rate-controlled dosage form of agent that is in communication with a liquid flowing through the chamber, and wherein when in operation, the means releases the agent into the liquid at a predetermined rate that is substantially independent of the volume rate of liquid flow flowing through the chanber; and,
(d) a conduit that communicates with the chamber outlet and extends to an infusion recipient site.

The agent formulation chamber generally comprises means for housing and delivering an agent at a rate-controlled by the means overtime.

BRIEF DESCRIPTION OF THE DRAWINGS

In the drawings, which are not drawn to scale, but are set forth to illustrate various embodiments of the invention, the Figures are as follows.

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 1:
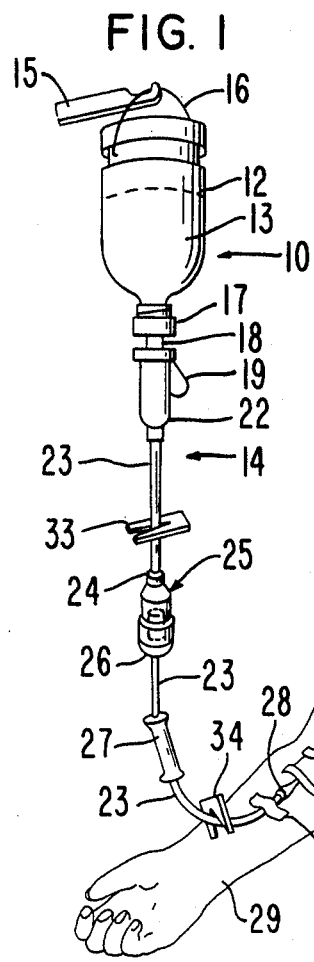
FIG. 1 is a perspective view showing an embodiment of the invention comprising an intravenous delivery system in use.

FIG. 1 illustrates an operative embodiment of the invention, comprising an intravenous delivery system, generally designated by the numeral 10. System 10 comprises a container 12 that contains a liquid 13 adapted for intravenous administration, and an administration set, generally designated 14. The liquid 13 in container 12 will typically be a medical fluid, a sterile solution such as an aqueous solution of dextrose, saline, and electrolytes. It must be a pharmaceutical vehicle for intravenous administration and for an agent that is to be administered to a recipient. Container 12 is manufactured from glass or plastic, and preferably of the no air-tube vacuum type and thus it is used with an administration set that has an air inlet filter. Other types of containers such as the air-tube vacuum type, or the non-vented type can be used for the intended purpose. These alternative containers do not require an air filter in the administration set. Container 12 can be rigid, semi-rigid or flexible in structure, and it is usually adapted to be hung neck-down from a hanger 15 by a handle or strap 16 that connects or surrounds container 12. The neck of container 12 is covered by a closure 17, generally made of rubber and air-tight.

Administration set 14 and container 12 are interconnected by piercing closure 17 with one end of a needle or hollow spike 18 attached to or formed as a part of administration set 14. Needle 18 is equipped with a side air vent 19. The other end of needle 18 is enlarged and fits snugly into a drip chamber 22. Drip chamber 22 traps air contained in the set and facilitates adjusting the flow rate of intravenous fluid 13 from container 12 as the flow proceeds drop wise. The outlet at the bottom of drip chamber 22 is connected to a first segment of tubing 23 which fits into inlet 24 of agent formulation chamber 25, the details of which are presented in subsequent figures. A second segment of tubing 23 connects to outlet 26 of agent formulation chamber 25 and leads to bacterial filter 27. A third segment of tubing 23 extends from filter 27 to an infusion agent receptor site, terminating in an adapter-needle assembly 28 that is inserted into a vein of warm-blooded animal 29, shown as a human patient's arm. An affixation means 32, usually a piece of tape, holds adapter-needle assembly 28 firmly in place on the recipient's arm. The administration set can also include a pair of tubing clamps 33 and 34 located on either side of formulation chamber 25 that may be used to govern or stop the flow rate of intravenous fluid through the intravenous therapy system.

Figure 2A:
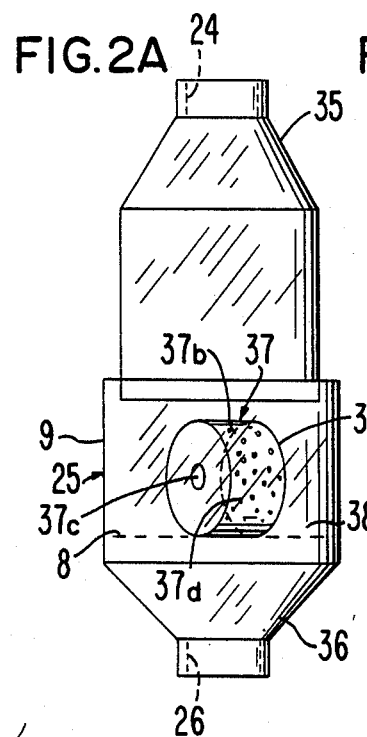
FIGS. 2a and 2b are perspective views of an agent formulation chamber provided by the invention with the formulation chamber housing a means for delivering an agent which means is manufactured as an agent delivery device.
Figure 2B:
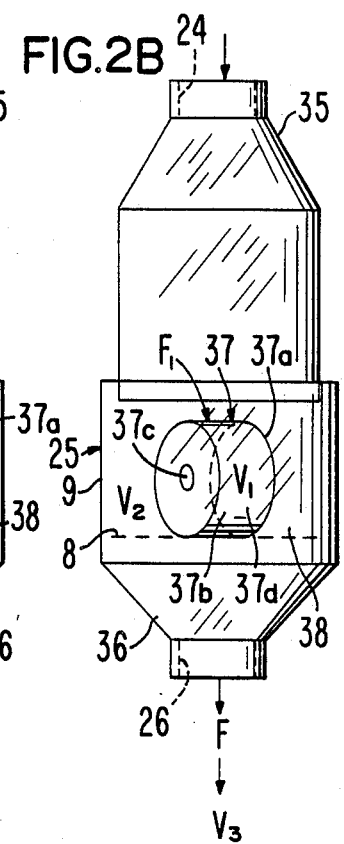

Agent formulation chamber 25, as seen in FIGS. 2A and 2B, is the unique component of the intravenous delivery system. Agent formulation chamber 25 is sized and adapted for use in intravenous systems, it is self-contained, self-powered and amenable to low cost manufacturing. The use of the agent formulation chamber with an agent delivery means therein does not require any reconstitution or admixture prior to use. Agent formulation chamber 25, hereafter referred to as chamber 25, in the illustrated embodiment, comprises a wall 9 that surrounds and defines an internal space 38. Chamber 25 has an inlet 24 adapted and sized for placing chamber 25 into an intravenous delivery system, and it has an outlet 26 also adapted and sized for placing the chamber in the system. Inlet 24 and outlet 26 are made for receiving tube 23. Chamber 25, is manufactured of glass, plastic or the like, and as illustrated it is made of a transparent material for illustrating its structure and a device housed therein. In the embodiment shown, chamber 25 comprises a pair of interfitting housing halves 35 and 36 for containing agent delivery device 37 within space or lumen 38. A retaining means 8 in housing 36 permits the passage of fluid, keeps device 37 in lumen 38, and it also prevents device 37 from blocking outlet 26. Agent delivery device 37, in the illustrated embodiment is an osmotic, rate-controlled solid dosage form as described by patentee Felix Theeuwes in U.S. Pat. No. 3,845,770. The osmotic device 37, seen in opened section, comprises a semipermeable wall, 37a, such as cellulose acylate, cellulose diacylate, cellulose triacylate, cellulose acetate, cellulose diacetate or cellulose triacetate, that surrounds and forms a compartment 37b. A passageway 37c extends through semipermeable wall 37a and communicates compartment 37b and the exterior of device 37. Compartment 37b contains an agent formulation 37d, represented by dots, which agent formulation exhibits an osmotic pressure gradient across wall 37a of device 37 against an external fluid that enters chamber 25. The agent formulation can comprise an agent that exhibits an osmotic pressure gradient, or the agent formulation can comprise a drug mixed with an osmotically effective solute, such as sodium chloride, potassium chloride and the like, that exhibit an osmotic pressure substantially greater than the fluid in the chamber 25. In operation, fluid that enters in the chamber 25 is imbibed through the semipermeable wall of the device into the compartment in a tendency towards osmotic equilibrium at a rate determined by the permeability of the wall and the osmotic gradient across the wall thereby producing a solution that is dispensed through the passageway at a rate controlled by the device over a prolonged period of time. The delivery of agent formulation 37d for homogenously blending with fluid in chamber 25, is controlled by device 37, and its rate of delivery is independent of the rate of fluid flow, and the pH of the fluid in the chamber. Device 37 maintains its physical and chemical integrity throughout its releasing history. In other embodiments, not shown, chamber 25 can be manufactured as a one-piece unit with the delivery device therein, or chamber 25 can be manufactured with a closable entrance for admitting the delivery device. Additionally, another embodiment of the invention comprises chamber 25 simultaneously acting as a drip chamber while housing the agent delivery device. In this embodiment the agent formulation chamber-drip chamber is used to achieve a desired fluid drop rate. For example, the agent formulation chamber-drip chamber can have a fast drop rate for adults, or it can have a slower drop rate for pediatric use. The agent formulation-drip chamber can be made with various sized inlets for controlling the rate of drip, or the drip can be controlled by a regulating clamp on the tubing conveying fluid thereto. The agent formulation chamber-drip chamber can deliver, for example from 2 to 75 drops per milliliter over from 1 minute to 1 hour. More preferrably, the therapist can adjust the rate of flow of 2 to 20 drops per minute, or for the need of the patient.

The rate performance of the delivery devices used in formulation chamber 25 for the purpose of the invention also can be described mathematically in terms of the physical and chemical composition of the agent release systems. Generally, delivery systems encompassed by this invention are those for which $Q_R \leqq 0.1 Q_{KVO}$, where $Q_{KVO}$ is the flow of fluid required to maintain flow into the veins of an animal in which the flow path terminates, by needle or catheter. This flow is referred to as the "keep vein open" rate, KVO, and it typically is for an adult patient about 10–20 drops per minute, or 0.5–1.0 ml per minute. $Q_R$ is the maximum rate of fluid flow needed for the delivery system to release agent in solution at its label rate. Thus, delivery systems for adult use require less than 0.05–0.1 ml/min to achieve label delivery rate, and show independence of delivery rate from flow at all higher flows are encompassed by this invention. Delivery systems for pediatric use will have a lower absolute limit, but still satisfy the general criterion of $Q_R \leqq 0.1 Q_{KVO}$.

During operation of device 37 as seen in FIG. 2B, the mass delivery rate of agent from chamber 25 is given by the volume flow rate F expressed by equation 1, of fluid entering chamber 25, times the concentration of agent $C_2$, in the chamber with a volume $V_2$. In the chamber, $V_2$ is the $$F = dV/dt \tag{1}$$

volume of the total chamber less the volume $V_1$ of agent delivery device 37. In the chamber, it is assumed that lumen $V_2$ is stirred by fluid flow to achieve a uniform concentration $C_2$. The chamber is designed to produce a steady state mass flow rate $dm_3/dt$, expressed in equation 2 independent of flow rate F leaving the chamber and conveyed to an agent recipient, represented by volume $V_3$. The calculations presented here are $$dm_3/dt = dV/dt \cdot C_2 \tag{2}$$

performed to determine the flow regimen for which the intended end result can be achieved over time. The calculations are for an osmotic device, designated as 37, containing a mass of agent $m_{10}$, at the start of a beneficial delivery program. During operation, the device delivers at a zero order rate as given by equation (3).

$$\frac{dm_1}{dt} = K_1 \frac{A_1}{h_1} (\pi_1 - \pi_2) S_1 \tag{3}$$

wherein: $K_1$ is the permeability of the wall of the delivery device to water, $A_1$ is the wall area of the device, $h_1$ is the thickness of the wall, $\pi_1$, is the osmotic pressure of saturated agent solution in the device, $\pi_2$ is the osmotic pressure of the solution in the lumen of the chamber at concentration $C_2$, and $S_1$ is the solubility of agent in volume $V_1$ in the device. The mass of agent $m_2$ in the lumen of the chamber at concentration $C_2$ is conveyed to the patient. The patient then has a total amount of agent infused of mass $m_3$ such that the mass balance at any time is given by equation 4.

$$m_{10} = m_1 + m_2 + m_3 \quad (4)$$

As a result, the mass change in each compartment, the device, the chamber and the patient, is expressed by equation 5, $$dm_1/dt + dm_2/dt + dm_3/dt = 0 \quad (5)$$

wherein $$dm_3/dt = FC_2 \quad (6)$$

since $$m_2 = V_2 \cdot C_2 \quad (7)$$

and it follows that $$\frac{dm_2}{dt} = V_2 \frac{dC_2}{dt} + C_2 \frac{dV_2}{dt} \quad (8)$$

$$\frac{dV_2}{dt} = 0, \quad (9)$$

it follows that $$\frac{dm_2}{dt} = V_2 \frac{dC_2}{dt} \quad (10)$$

From equations (3), (5), (6) and (10), equation (11) follows:

$$V_2 \frac{dC_2}{dt} = \frac{K_1}{h_1} A_1 (\pi_1 - \pi_2) S_1 - F \cdot C_2 \quad (11)$$

where $\pi_2$ and $C_2$ are related through Van Hoff's law as shown by 12:

$$2/1 = C_2/S_1 \quad (12)$$

Equations (11) and (12) result in differential equation 13, from which $C_2$ follows as a function of time.

$$V_2 \frac{dC_2}{dt} = K_1 \frac{A_1}{h_1} \pi_1 \cdot S_1 - K_1 \frac{A_1}{h_1} \pi_1 C_2 - F \cdot C_2 \quad (13)$$

and when equation (14) is substituted therein, $$F_1 = K_1 \frac{A_1}{h_1} \cdot \pi_1 \quad (14)$$

equations (15) and (16) follow, $$V_2 \frac{dC_2}{dt} = F_1 S_1 - F_1 C_2 - FC_2 \quad (15)$$

$$\frac{dC_2}{dt} + \frac{(F_1 + F)}{V_2} C_2 = \frac{F_1 S_1}{V_2} \quad (16)$$

and for (16) the solution is given by equation (17).

$$C_2 = \frac{F_1 S_1}{F_1 + F} \left[ 1 - \exp - \left( \frac{F_1 + F}{V_2} \right) \cdot t \right] \quad (17)$$

Equation (17) indicates the time course in which $C_2$ attains its steady state value. The steady state value is given by 18, with the flow rate $$C_2 = \frac{F_1 S_1}{F_1 + F} \quad (18)$$

The flow rate into the patient is obtained from (17) and (2) as equation (19).

$$\frac{dm_3}{dt} = F \cdot \frac{F_1 \cdot S_1}{F_1 + F} \left[ 1 - \exp - \left( \frac{F_1 + F}{V_2} \right) \cdot t \right] \quad (19)$$

Figure 14:
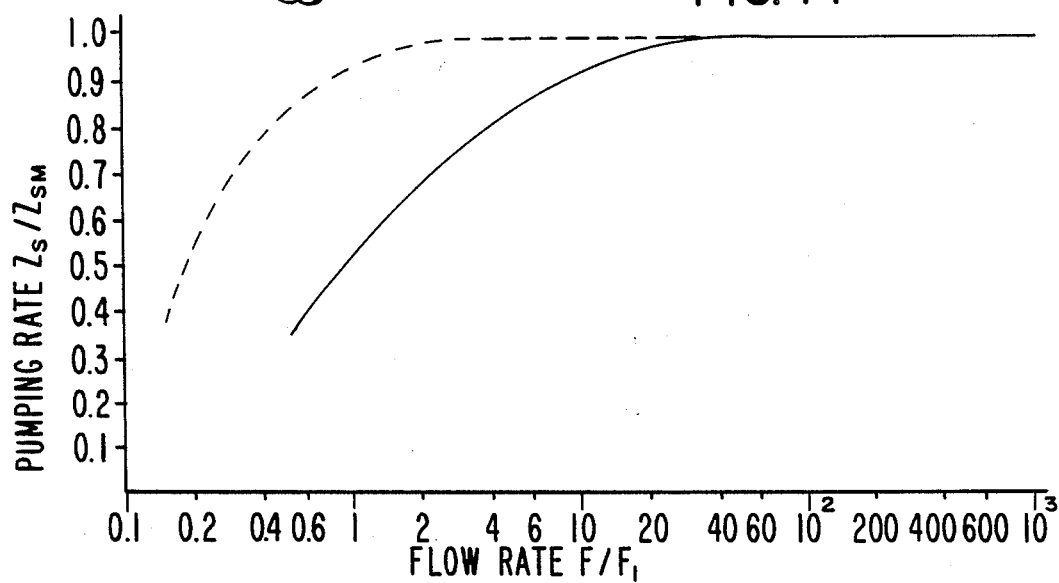
FIG. 14 is a graph showing a typical relationship between the mass rate of agent administration and the volume flow rate of intravenous fluid to the patient that results from use of the invention; and, FIG. 15 is a graph that indicates the time required for the delivery rate to reach a steady state of delivery.

Equation 19 leads to (1) the minimum flow rate $F_m$ needed to achieve a regimen independent of flow, and (2) the time it takes until the patient receives steady state intravenous administration. The steady state flow rate achieved with the infuser is given by equation 20 or 21, $$\frac{dm_3}{dt_s} = Z_s = F \cdot \frac{F_1 \cdot S_1}{F_1 + F} \quad (20)$$

$$Z_s = \frac{F_1 S_1}{1 + \frac{F_1}{F}} \quad (21)$$

and the maximum steady state flow rate is the steady state expressed by equation 22, $$Z_{sm} = F_1 S_1 \quad (22)$$

the delivery rate from the delivery device. The steady state flow rate as a function of flow F is given by equation 23

$$\frac{Z_s}{Z_{sm}} = \frac{1}{1 + \frac{F_1}{F}} \quad (23)$$

and graphically represented in FIG. 14, solid line, as a function of $F/F_1$, wherein it can be seen at high flow rates $F > F_1$, the agent delivery rate from the device is independent of fluid flow in the chamber.

Generally, the volume flow rates from an osmotic device delivering at high rates, for example 100 mg/hr, are on the order of 0.05 to 0.2 ml/hr. The incoming fluid rate from a container containing a medical liquid, and referred to as the drip rates from an intravenous gravity feed system are in the range of from 1 to 400 ml/hr, and for these two ranges the total mass delivery rate is within 80 percent of the designed rate at all times.

The steady state rate of equation (20) can be expressed relative to the non-steady state rate of equation (19) by equation 24.

$$\frac{1}{Z_s} \cdot \frac{dm_3}{dt} = \left[ 1 - \exp - \left( \frac{F_1 + F}{V_2} \right) \cdot t \right] \quad (24)$$

Under operating conditions, $F > F_1$, equation (24) can be expressed as equation (25), and $$t = \frac{-V_2}{F} \cdot \ln \left[ 1 - \frac{1}{Z_s} \frac{dm_3}{dt} \right] \quad (25)$$

$V_2/F$ is a characteristic time of the chamber. It is the time it takes to clear volume $V_2$ at incoming flow rate F.

Figure 15:
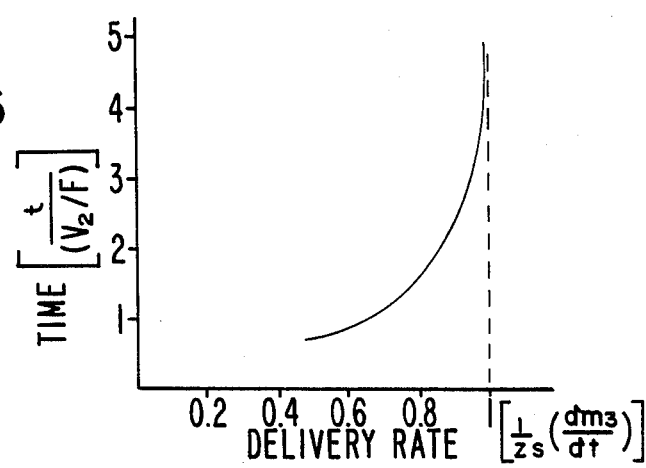

These systems are typically designed such that this time is small to reduce the start up time, and the dead volume $V_2$ in the chamber is small compared to the volume transported in the start up time. The dead volume $V_2$ is usually less than 1 ml. Thus, for the minimum flow rate of 1 ml/hr used in intravenous therapy, the characteristic time would be one hour. Accompanying FIG. 15 represents the time it takes to achieve any fraction of a steady state value in units of characteristic time, and generally indicating 80 percent of the steady state rate is achieved in 1.5 times the characteristic time.

Figure 3:
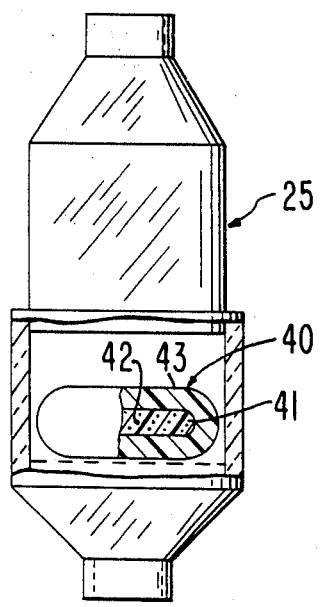
FIG. 3 is a view of an agent formulation chamber containing an agent delivery device comprising an agent release rate controlling membrane surrounding a reservoir containing agent.

FIG. 3 depicts agent formulation chamber 25, in opened section, containing another device 40 for delivering an agent into an intravenously acceptable fluid that enters chamber 25. Device 40 is illustrated in opened-section and it comprises an inner mass transfer conductor 41, illustrated as a solid core and formed of a polymeric material such as cured polydimethylisoxane, with agent 42 dispersed therethrough. Surrounding mass transfer conductor 41 is an agent release rate controlling membrane 43, preferably formed of a polymeric material, such as polyethylene. Both conductor 41 and membrane 43 are permeable to the passage of agent 42 by diffusion, that is, agent can dissolve in and diffuse through conductor 41 and membrane 43. However, the permeability of conductor 41 is greater than that of membrane 43, and membrane 43 thus acts as the rate controlling member for agent release from device 40. Device 40 maintains its physical and chemical integrity throughout the period of agent delivery. Agent delivery device 40 is disclosed in U.S. Pat. No. 3,854,480.

Figure 4:
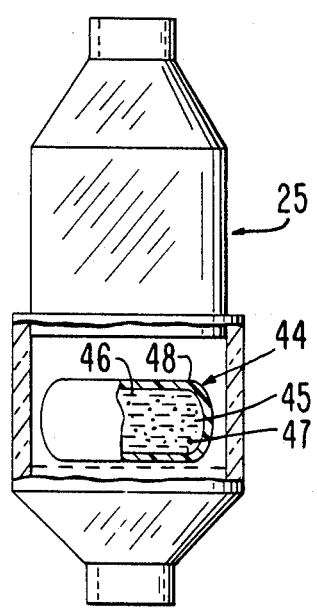
FIG. 4 is a view of an agent formulation chamber containing a delivery device comprising a release rate controlling membrane surrounding a different reservoir containing agent.

FIG. 4 illustrates the agent formulation chamber, with a section of its wall removed, housing delivery device 44 for delivering an agent at a rate controlled by device 44 into a fluid that enters chamber 25. Device 44 is seen in opened-section and it comprises a reservoir 45 formed of a liquid mass transfer conductor 46 such as a medical oil liquid carrier, permeable to the passage of agent, containing agent 47 such as the drug phenobarbital. Reservoir 45 is surrounded by a wall 48 formed of an agent or drug release rate controlling material permeable to the passage of agent 47, such as a polyolefin. The rate of passage of agent 47 is lower than the rate of passage through conductor 46, so that agent release by wall 48 is the agent release rate controlling step for releasing agent 47 from device 44. Device 44 maintains its physical and chemical integrity throughout its agent release history. Agent delivery device 44 is disclosed in U.S. Pat. No. 3,993,073, which patent is incorporated herein.

Figure 5:
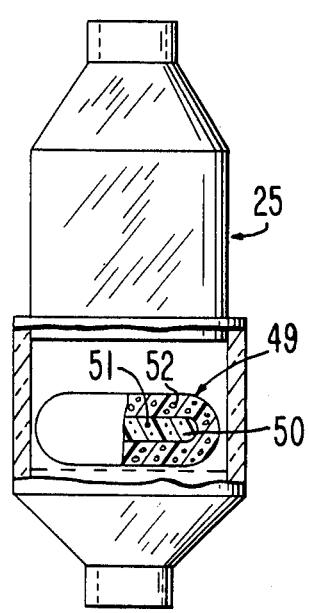
FIG. 5 is a view of an agent formulation chamber containing a delivery device comprising a microporous membrane surrounding a reservoir containing agent.

FIG. 5 illustrates agent formulation chamber 25, with a part of its wall removed, housing another device 49 for delivering an agent into a liquid that enters chamber 25 for forming an intravenously acceptable agent formulation. Device 49 is seen in opened-section and it comprises a wall 52 surrounding a reservoir 50 containing agent 51. The reservoir is formed of a solid carrier permeable to the passage of agent such as cured polydimethylsiloxane containing the drug diazepam. Wall 52 is formed of a microporous material, the pores of which contain an agent release rate controlling medium permeable to the passage of agent 51, for example, formed of a microporous polymer made by coprecipitation of a polycation and a polyanion. The release of agent 51 is controlled by device 49, which device maintains its physical and chemical integrity during the period of time it is in chamber 25. Device 49 is disclosed in U.S. Pat. No. 3,993,072, which patent is incorporated herein by reference.

Figure 6:
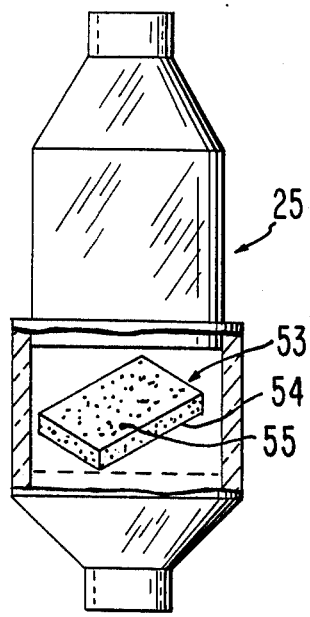
FIG. 6 is a view of an agent formulation chamber containing a delivery device comprising a matrix containing agent.

FIG. 6 is a view of formulation chamber 25 having part of its housing removed and housing device 53 for delivering an agent into a medical fluid that enters chamber 25 for forming in situ an intravenously acceptable agent formulation solution. Device 53 comprises a matrix 54 containing agent 55 distributed therethrough. Matrix 55 is formed from a polymeric material that is non-erodible, that is, it keeps its physical and chemical integrity over time, and it is permeable to the passage of agent 55 by the process of diffusion. The rate of agent release from the matrix is determined by the rate the agent dissolves in and passes through the matrix by diffusion, so that from the matrix it is the agent release rate controlling step. The matrix can possess any shape such as rod, disc and the like that fits into chamber 25. The polymers include polyolefins such as polyethylene containing muscle relaxants and the like. Materials useful for manufacturing the devices are disclosed in U.S. Pat. No. 3,921,636.

Figure 7:
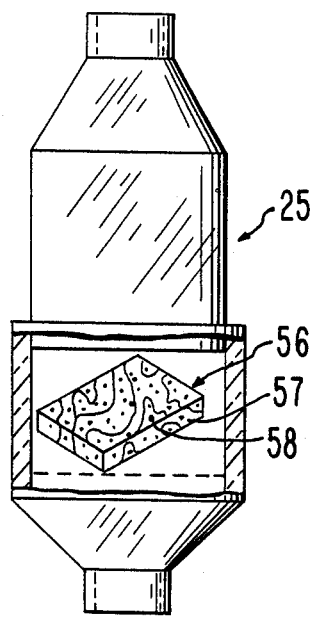
FIG. 7 is a view of an agent formulation chamber containing an agent delivery device comprising a microporous matrix containing an agent.

FIG. 7 is a view of agent formulation chamber 25, in opened view, housing device 56 for delivering an agent into a fluid that enters chamber 25. Device 56 is seen in opened section, and it is formed of a microporous polymeric material 57 containing agent 58 distributed therethrough. Matrix 57 is formed of a non-toxic, inert polymer, that is non-erodible and has a plurality of micropores for releasing agent at a controlled rate to fluid entering chamber 25. Microporous materials useful for the present purpose are disclosed in U.S. Pat. Nos. 3,797,494 and 3,948,254.

Figure 8:
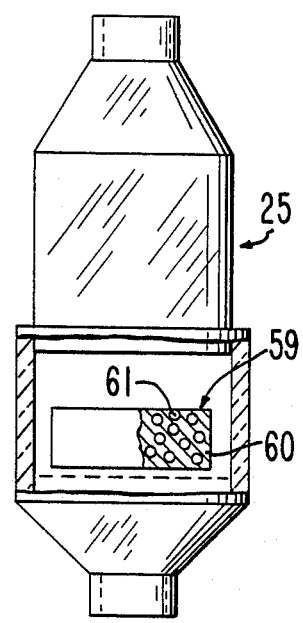
FIG. 8 is a view of an agent formulation chamber containing a delivery device comprising depots of agent.

FIG. 8 illustrates agent formulation chamber 25, in opened view, housing device 59 for delivering an agent into a medical fluid that enters chamber 25. Device 59 is seen in opened section and it comprises depots of agent solute 61 dispersed in and surrounded substantially individually by a polymer 60 that is impermeable to the passage of agent solute and permeable to the passage of fluid that enters chamber 25. Agent or a medication solute 61 exhibits an osmotic pressure gradient across the polymer against fluid that enters chamber 25. Agent 61 is released at a controlled rate by fluid from the chamber being imbibed through the polymer into the depots to dissolve the solute and generate a hydrostatic pressure in the depots, which pressure is applied against the wall of the depots thereby forming apertures that release the agent at a controlled rate over time. Polymer 60 is non-erodible, and device 59 can be shaped as a matrix, a rod, a disc, or like shapes. Procedures and materials useful for manufacturing osmotic bursting delivery systems are described in U.S. Pat. No. 4,177,256.

Figure 9:
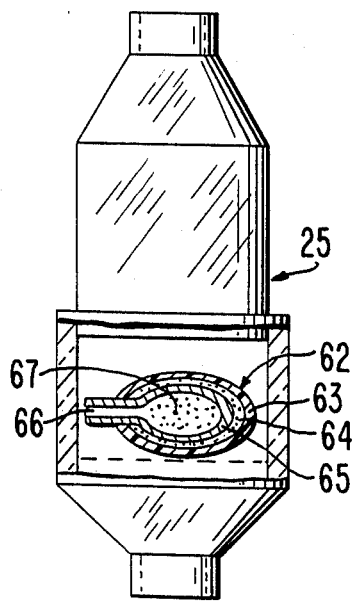
FIG. 9 is a view of an agent formulation chamber containing a delivery device comprising a housing and driving member surrounding a flexible container.

FIG. 9 illustrates agent formulation chamber 25, in opened view, containing device 62 useful for delivering an agent into a medically acceptable fluid passing through chamber 25. Device 62 is seen in opened view and it comprises an exterior wall 63 formed of a semipermeable polymer permeable to fluid and substantially impermeable to the passage of agents and solutes. A layer 64 of an osmotically effective solute, for example sodium chloride, is deposited on the inner surface of wall 63. Solute layer 64 surrounds an inner container 65 formed of a flexible material that is impermeable to solute and agent. Container 65 has a passageway 66 for delivering an agent 67 into a fluid in chamber 25. Device 62 dispenses agent by fluid permeating from chamber 25 through the outer wall 63 to continuously dissolve solute 64 in a tendency towards osmotic equilibrium, thereby continuously increasing the volume between wall 63 and container 65. This increase causes container 65 to continuously collapse and dispense agent 67 from device 62 at a controlled rate through passageway 66 to fluid passing through chamber 25. Osmotically powered agent dispensing devices are disclosed in U.S. Pat. Nos. 3,760,984 and 3,995,631.

Figure 10:
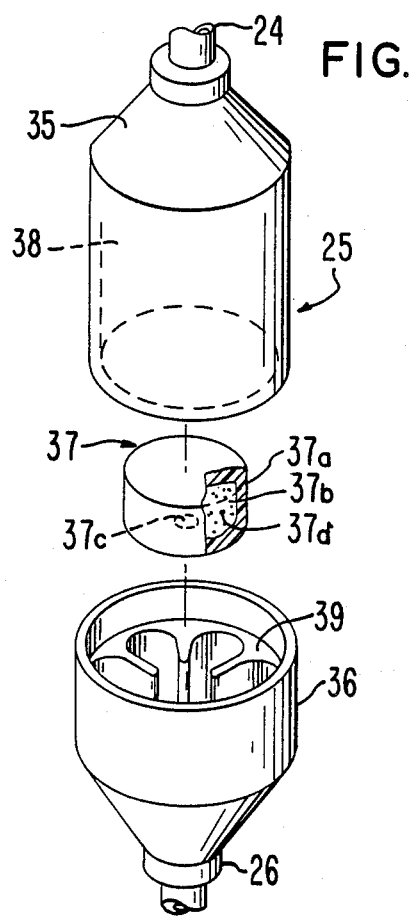
FIG. 10 is an embodiment of the invention illustrating an agent formulation chamber in fragmentary view.
Figure 11:
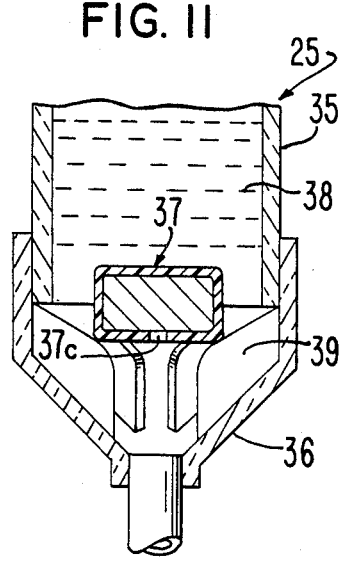
FIG. 11 is a sectional, fragmentary view of the parts of the embodiment shown in FIG. 10.

In FIGS. 10 and 11 another chamber 25 provided by the invention is seen composed of a pair of interfitting housing halves 35, 36 and a rate controlled solid agent or drug dosage form 37 contained within the lumen 38 of chamber 25. The chamber inlet 24 is in this embodiment the cone-shaped of housing half 35, and the chamber outlet 26 is in the cone-shaped end of half 36. The inside perimeter of half 36 has a series of downwardly inclined flutes 39 on which dosage form 37 rests. The dosage form is supported by the flutes above the outlet, and is thus kept from blocking the outlet. Dosage form 37 is an osmotic, rate-controlled dosage form as described above and in U.S. Pat. No. 3,845,770, which disclosure is incorporated herein by reference. In the illustrated embodiment, dosage form 37 has passageway 37c oriented in the direction of fluid flow through chamber 25 for lessening the incidence of membrane polarisation and to produce release rates practically unaffected by effluent agent. In this operation, the release pattern is seen in FIG. 14 as represented by the dashed lines. Another osmotic agent delivery device, not shown, that can be positioned in chamber 25 is disclosed by patentee Felix Theeuwes in U.S. Pat. No. 4,111,202, which patent is incorporated herein by reference. The device of this patent comprises a semipermeable wall that surrounds a first and second compartment with the first compartment containing an agent and the second compartment containing an osmotically effective solute that exhibits an osmotic pressure gradient across the semipermeable wall. In this device, the compartments are separated by a flexible membrane, and the device has a passageway that communicates with the compartment containing the agent for its delivery from the device. This device, when in operation, delivers agent by imbibing fluid from the infuser into the first compartment to form a solution containing agent, and into the second compartment to form a solution containing the solute which continuously fill the second compartment and expands the membrane into the first. The agent is delivered through the passageway by the combined actions of the first and second compartments at a controlled rate over a period of time. For this delivery device, like the device described above, the mass rate of agent released by the device is substantially independent of the volume flow of intravenous fluid to the patient as it is instead controlled by the mass release of agent from the dosage device. This relationship is shown in FIG. 14, in solid line. In FIG. 14 the rate of release from the device when passageway 37c is directed in the path of liquid flow is illustrated in dashed lines.

Agent administration that is independent of intravenous fluid flow rate is extremely advantageous since careful control of the volume flow rate of intravenous fluid through the formulation chamber is not required. Hence, repeated adjustment of the flow by medical personnel, or the use of expensive, automated flow monitors is not needed. The operation also has all the advantages that are associated with the fact that the formulation of agent and intravenous fluid is carried out automatically in situ within the chamber. Moreover, since the chamber can be positioned within the intravenous therapeutic system when needed, the separation of the agent and the intravenous fluid until administration provides significant stability and handling advantages. The present invention also eliminates the need to have the agent formulated into a parenteral solution by a pharmacist, and, it also eliminates the need for the agent to be packaged separately from the intravenous fluid container. Another advantage provided by this invention, is since the agent dosage delivery device is compatible with conventional sterilization techniques that are commonly used to sterilize intravenous therapy systems, the agent formulation chamber, including the agent delivery device, may be incorporated into the entire intravenous system at the time of manufacture and sterilized therewith.

The invention also provides that agent delivery devices each containing various amounts of an agent or an amount of drug can be placed into the formulation chamber. The device can contain from about 1 mg to 5 g of agent, or more, in for example 1 to 7 or more dosage units. The device can release agent at a rate of 10 ng/hr up to 3 g/hr into the chamber having a volume capacity of at least 2 ml up to 250 ml, through which intravenous fluid flows at a rate of 1 ml/hr up to 20 ml/hr or higher. The term drug is represented by heparin, isoproterenol, and the like.

Figure 12:
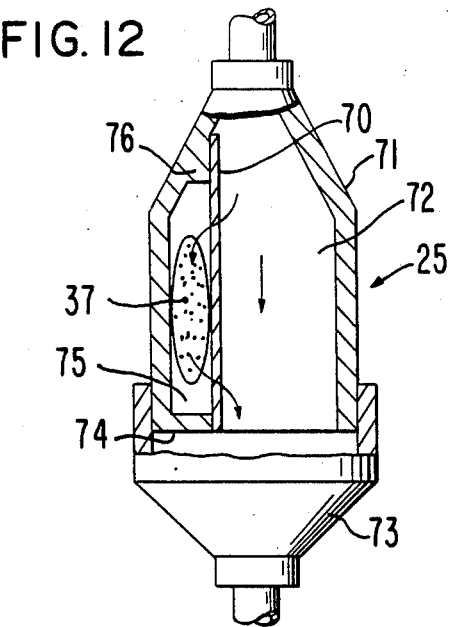
FIG. 12 is an enlarged, partly sectional view of another formulation chamber.

FIG. 12 illustrates another agent formulation chamber designated 25. In this chamber, the rate-controlled dosage delivery device is not in direct path of the intravenous fluid flow through chamber 25. In this embodiment chamber 25 includes a pair of hollow interfitting housing halves 71 and 73. Housing half 71 has an inlet opening or its cone-shaped end for tubing 23. The inner surface of half 71 carries a pair of integral flanges 74 and 76 that together with a thin microporous membrane 70 define an enclosed pocket 75 inside the lumen 72 of chamber 25. An agent delivery device 37 is contained within the pocket. Device 37 is, as described above, a complete rate-controlled form and it may additionally act in combination with membrane 70 to enhance the control of agent into passing fluid. Such combinations, in which an element of chamber is used with a delivery device are intended to be within the phrase rate-controlled delivery as used herein. In such combinations, membrane 70 can serve as a rate-controlling barrier that regulates the rate at which the agent enters the mainstream of intravenous fluid flow through the chamber. Since device 37 is a complete rate-controlled form, the membrane acts as a supplemental barrier or as a means for confining the device so that it does not block the entrance or exit of chamber 25. Membrane 70 permits the passage of fluid so that as intravenous fluid fills and passes through the chamber, which flow is represented by the straight arrow in FIG. 12, water from the fluid will diffuse, represented by curved arrows, through the pores of the membrane into the pocket and motivate device 37 to release drug. The released agent will pass from the pocket through the membrane into the mainstream flow through chamber 25. The rate at which the agent will enter the mainstream will depend on its concentration in the solution within the pocket, the surface area of membrane 70, and the rate of passage of the membrane to agent. In any event, that rate is independent of the overall flow rate of intravenous fluid through chamber 25. Accordingly, the agent is formulated in situ within chamber 25 and it is administered to the patient at a rate that is dependent upon the characteristics of the device. The microporous membrane 70 may be useful also to prevent agent particles from entering the flow path, and for providing an extra margin of safety against microorganisms, in the event any may have survived the sterilization procedure for the system.

Figure 13:
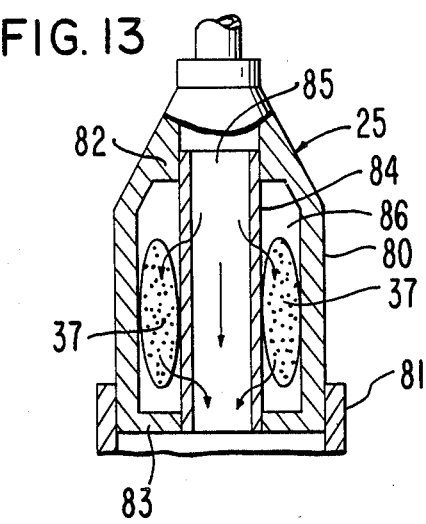
FIG. 13 is an enlarged, partly sectional view of still another embodiment of an agent formulation chamber housing a delivery device.

FIG. 13 shows another agent formulation chamber, generally designated 25, in which the dosage form is not in the direct path of the intravenous fluid flow through the chamber. The chamber is particularly adapted to hold a plurality of the same or different delivery devices. The chamber, like those shown in the other figures, includes a pair of hollow, interfitting housing halves 80 and 81, that have an inlet opening and outlet opening, not shown, at their respective ends. The inside surface of half 80 carries a pair of radial flanges 82 and 83, that extend entirely around the inner circumference of the half. These flanges, together with a tubular microporous membrane 84 that is attached at its ends to the flanges, divides the lumen of the chamber into a main intravenous flow path 85 and an outer concentric pocket 86. A plurality of agent delivery units 37 are contained within the pocket. Membrane 84 and pocket 86 function in the same manner as membrane 70 and pocket 75 of FIG. 12. That is, an intravenous fluid flows through the chamber, water from the fluid diffuses through the membrane into pocket 86 and causes the device to release agent. The agent then diffuses from the pocket through the membrane and into the mainstream of the intravenous fluid flow. In instances in which the devices are different, it may be desirable to divide pocket 86 into a plurality of pockets, one for each device. This may be accomplished with impermeable axial partitions, not shown, that extend between the inner surface of the half, the membrane, and the two flanges. In such instances it may be also desirable to have membrane 84 formed from segments of different microporous materials, each segment covering a separate pocket. In this manner different release rates of different agents into the passing intravenous fluid may be effected.

This novel invention uses means for the obtainment of precise control of agent release into an intravenous therapeutic system. While there has been described and pointed out features of the invention as applied to presently preferred embodiments, those skilled in the art will appreciate that various modifications, changes, additions, and omissions in the system illustrated and described can be made without departing from the spirit of the invention.

I claim:

1. An intravenous delivery system for administering an agent formulation intravenously to a human in which the agent formulation is formulated in situ comprising in combination:
   (a) a container of a pharmaceutically acceptable intravenous fluid that is a carrier for the agent;
   (b) an intravenous administration set connected to the container for permitting the fluid to flow from the container through the administration set, the set comprising;
       (1) a drip chamber;
       (2) a tubing extending from the drip chamber to a human; and,
       (3) an agent formulation chamber connected into the tubing such that the intravenous fluid flows through the formulation chamber, the formulation chamber comprising a hollow housing and a rate controlled dosage means that maintains its physical and chemical integrity within the housing that is in communication with the fluid flowing through the chamber and that releases agent into the fluid at a predetermined rate.

2. The intravenous delivery system according to claim 1 wherein a skin piercing means is connected to the tubing for administering the agent formulation to the human.

3. The intravenous delivery system according to claim 1 wherein the rate controlled dosage means is a solid and it releases agent at a rate that is independent of the volume rate of intravenous fluid flow through the formulation chamber.

4. The intravenous therapy system according to claim 1 wherein the formulation chamber additionally contains a filter member.

5. The intravenous delivery system according to claim 1 wherein the formulation chamber includes means for preventing the dosage means from blocking the flow of intravenous liquid through said chamber.

6. The intravenous delivery system according to claim 1 wherein the formulation chamber includes an inner enclosed pocket at least partly defined by a membrane, the membrane being the interface between the pocket and the main flow path of the fluid through said chamber, and the rate-controlled dosage means comprises a combination of the membrane and a dosage means within the pocket, whereby fluid from the intravenous fluid diffuses through the membrane into the pocket, and a solution of agent diffuses from the pocket through the membrane into the mainstream of intravenous flow through said chamber.

7. The intravenous delivery system according to claim 6 wherein the membrane is in the form of a hollow tube that extends axially through the formulation chamber, the tube defining the main flow path of intravenous fluid through said chamber, and the pocket being concentric to the main flow path defined by the outer surface of the tube and the inner surface of the housing.

* * * * *